US 7,394,535 B1

(12) United States Patent
Chen et al.

(10) Patent No.: US 7,394,535 B1
(45) Date of Patent: Jul. 1, 2008

(54) OPTICAL METROLOGY USING A PHOTONIC NANOJET

(75) Inventors: Zhigang Chen, San Jose, CA (US);
Hanyou Chu, Palo Alto, CA (US);
Shifang Li, Pleasanton, CA (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 11/726,083

(22) Filed: Mar. 20, 2007

(51) Int. Cl.
*G01N 21/00* (2006.01)

(52) U.S. Cl. ............... 356/237.4; 356/237.2; 356/237.3; 356/445; 356/342

(58) Field of Classification Search ... 356/237.2–237.6, 356/445–448, 612, 342
See application file for complete search history.

(56) References Cited

OTHER PUBLICATIONS

Chen et al., U.S. Appl. No. 11/726,076, "Automated Process Control Using Optical Metrology With A Photonic Nanojet", filed Mar. 20, 2007.*
Owen, J. F. et al. (Nov. 1981). "Internal Electric Field Distributions of a Dielectric Cylinder at Resonance Wavelengths,". *Optics Letters* 6(11):540-542.
Benincasa, D. S. et al. P. (Apr. 1987). "Spatial Distribution of the Internal and Near-Field Intensities of Large Cylindrical and Spherical Scatterers," *Applied Optics* 26(7):1348-1356.
Xu. Y. (Jul. 1995). "Electromagnetic Scattering by an Aggregate of Spheres," *Applied Optics* 34(21):4573-4588.
Adler, C. L. et al. (Jun. 1997). "High-Order Interior Caustics Produced in Scattering of a Diagonally Incident Plane Wave by a Circular Cylinder," *Journal of the Optical Society of America A* 14(6):1305-1315.
Lock, J. A. et al. (Oct. 2000). "Exterior Caustics Produced in Scattering of a Diagonally Incident Plane Wave by a Circular Cylinder: Semiclassical Scattering Theory Analysis," *Journal of the Optical Society of America A* 17(10):1846-1856.
Chen, Z. et al. (Apr. 5, 2004). "Photonic Nanojet Enhancement of Backscattering of Light by Nanoparticles: a Potential Novel Visible-Light Ultramicroscopy Technique," *Optics Express* 12(7):1214-1220.
Chen, Z. et al. (Jan. 15, 2006). "Superenhanced Backscattering of Light by Nanoparticles," *Optics Letters* 31(2):196-198.
May, G. S. et al. (2006). *Fundamentals of Semiconductor Manufacturing and Process Control*. John Wiley & Sons, Inc.: Hoboken, New Jersey, 13 pages.
U.S. Appl. No. 11/726,076, filed Mar. 20, 2007.

* cited by examiner

*Primary Examiner*—L. G. Lauchman
*Assistant Examiner*—Rebecca C Slomski
(74) *Attorney, Agent, or Firm*—Morrison & Foerster LLP

(57) ABSTRACT

An inspection area on a semiconductor wafer can be examined using a photonic nanojet. The photonic nanojet, an optical intensity pattern induced at a shadow-side surface of a dielectric microsphere, is generated. The inspection area is scanned with the photonic nanojet. A measurement is obtained of the retroreflected light from the dielectric microsphere as the photonic nanojet scans the inspection area. The existence of a structure in the inspection area is determined with the obtained measurement of the retroreflected light.

20 Claims, 9 Drawing Sheets

OPTICAL METROLOGY USING A PHOTONIC NANOJET

BACKGROUND

1. Field

This application generally relates to optical metrology and more particularly to examining an inspection area of a semiconductor wafer with a photonic nanojet.

2. Related Art

With the current drive towards smaller geometries of integrated circuit (IC) devices, measurement of IC device features is increasingly difficult as the features become smaller. Optical microscopy and spectroscopy technologies are well established. However, there are fundamental limitations of conventional optical microscopy. In the case of imaging objects with optical fields propagating in the far-field zone, the fundamental constraint is the diffraction of light that limits conventional optical microscopy to a spatial resolution comparable to one-half wavelength, or about 200 nm for visible light. As problems of interest push further into the nanometric regime, the importance of imaging techniques that allow nanoscale resolution or sensitivity has been steadily increasing.

Near-field optical techniques making use of the evanescent field have been developed to overcome the diffraction limit of far-field optics. In particular, a proximal-probe technique called near-field scanning optical microscopy (NSOM) has extended the range of optical measurements beyond the diffraction limit and stimulated interest in many disciplines, especially material and biological sciences. However, the low light-collection efficiency, relatively slow image-acquisition rate, and inability to image or sense objects below the surface of NSOM fundamentally limit its utility.

SUMMARY

In one exemplary embodiment, a photonic nanojet, an optical intensity pattern induced at a shadow-side surface of a dielectric microsphere, is generated. An inspection area of a semiconductor wafer is scanned with the photonic nanojet. A measurement is obtained of the retroreflected light from the dielectric microsphere as the inspection area is scanned with the photonic nanojet. The existence of a structure in the inspection area is determined with the obtained measurement of the retroreflected light.

DETAILED DESCRIPTION

In order to provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

Figure 1:
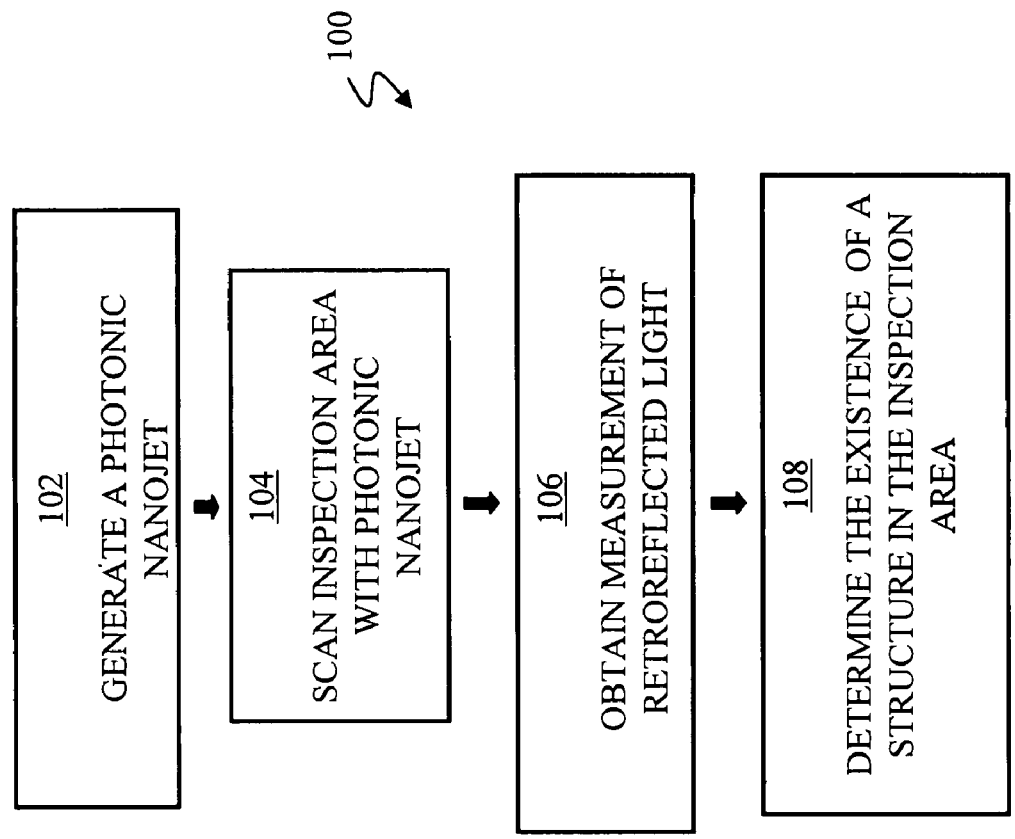
FIG. 1 is a flow diagram illustrating an exemplary process of determining the existence of a structure in an inspection area of a semiconductor wafer using a photonic nanojet.

FIG. 1 is a flow diagram of an exemplary process of examining an inspection area of a semiconductor wafer. In step 102, a photonic nanojet, an optical intensity pattern induced at a shadow-side surface of a dielectric microsphere, is generated. See "Generation of Photonic Nanojets" section below for further discussion of this step.

In step 104, the inspection area is scanned with the photonic nanojet. The inspection area can be scanned by moving the photonic nanojet relative to the wafer, moving the wafer relative to the nanojet, or moving both the wafer and the nanojet relative to each other. The wafer can be moved using a moving stage. The nanojet can be moved using an actuator. Fine movement of the wafer and/or the nanojet can be achieved with a piezo nanopositioning system or other similar system.

It should be recognized that the inspection area can be scanned by continuous or discrete movement of the wafer and/or nanojet. For example, the inspection area can be scanned by continuously moving the nanojet over the inspection area. Alternatively, the inspection area can be scanned by moving the nanojet to one location in the inspection area, stopping over the location in the inspection area, then moving the nanojet to another location in the inspection area.

In step 106, a measurement of retroreflected light is obtained from the dielectric microsphere as the inspection area is scanned with the photonic nanojet. In particular, as the photonic nanojet interacts with the wafer surface, a portion of incoming light is retroreflected from the dielectric microsphere. The retroreflected light can be measured using a detector, which can include photodiodes, photomultipliers, or other monochromator-based devices.

In step 108, the existence of a structure in the inspection area is determined with the obtained measurement of the retroreflected light. In particular, a measured backscattered signature can be generated with the measurement of retroreflected light. When the nanojet encounters a structure in the inspection area, a change of several orders-of-magnitude in the backscattered signature can be observed. Thus, the existence of a structure can be determined by comparing the measured backscattered signature to a previously obtained backscattered signature without a structure in the nanojet. Alternatively, the measured backscattered signature can be compared to a library of backscattered signatures, which were simulated or measured with and without a structure in the nanojet. If the measured backscattered signature matches with a backscattered signature from the library that was simulated or measured with a structure in the nanojet, then a structure is determined to exist. If the measured backscattered signature matches with a backscattered signature from the library that was simulated or measured without a structure in the nanojet, then a structure is determined not to exist.

The structure can be any isolated, nonperiodic, or periodic structure formed on the semiconductor wafer, such as a gate, line, contact hole, via, drain, periodic structure, and the like. Additionally, the structure can be foreign matter, such as a contaminating particle. By determining the existence of the structure, the fabrication process can be evaluated. For example, if a structure is intended to be formed in a specific location on the wafer, the specific location can be examined to determine if the structure exists. If the structure does not exist, then a fault in the fabrication process can be detected. Alternatively, if a specific location on the wafer should be unpatterned, then the specific location can be examined to determine if a structure, including a contaminating particle, exists. If the structure exists, then a fault in the fabrication process or contamination of the fabrication process can be detected.

In addition to determining the existence of a structure in the inspection area, in one exemplary embodiment, the height and width of the structure can be determined with the obtained measurement of the retroreflected light. As discussed above, the measured backscattered signature can be generated with the measurement of retroreflected light. The measured backscattered signature can include backscattering intensity. As discussed below, the enhanced backscattering intensity (difference between backscattering intensity with and without a structure in the nanojet) is proportional to the third power of a structure's height and width. Thus, the height and width of a structure can be determined based on the enhanced backscattering intensity.

In a library-based process, the height and width of a structure can be determined by comparing the measured backscattered signature to a library of backscattered signatures corresponding to structures of varying heights and widths. More specifically, each backscattered signature in the library is associated with a structure with a particular height and width. When a match is made between the measured backscattered signature and one of the backscattered signatures in the library or when the difference of the measured backscattered signature and one of the backscattered signatures in the library is within a preset or matching criterion, the height and width of the structure corresponding to the matching backscattered signature in the library is presumed to be the actual height and width of the structure. The backscattered signatures in the library can be simulated or previously measured for structures with varying heights and widths.

Additionally, the location of the structure can be determined. In particular, the position of the nanojet on the wafer can be determined from a positioning system used in conjunction with moving the nanojet and/or the wafer. Thus, when the existence of the structure is determined, the position of the nanojet on the wafer can be used to determine the location of the structure.

Figure 9C:
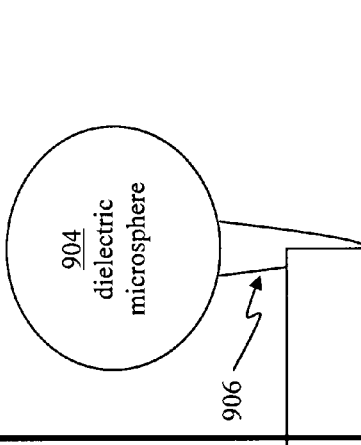
FIGS. 9a-c illustrate a photonic nanojet scanning a structure that is wider than the photonic nanojet.
Figure 9B:
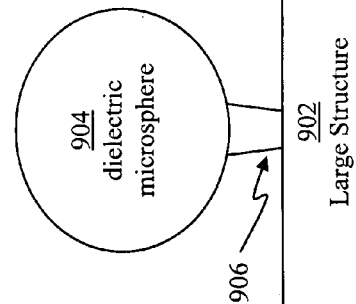
Figure 9A:
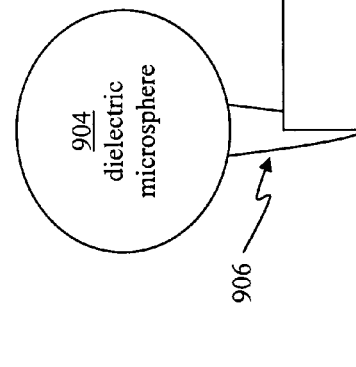
Figure 10C:
FIGS. 10a-c illustrate the corresponding graphs of the measured backscattered signatures from the FIGS. 9a-c photonic nanojet positions.
Figure 10B:
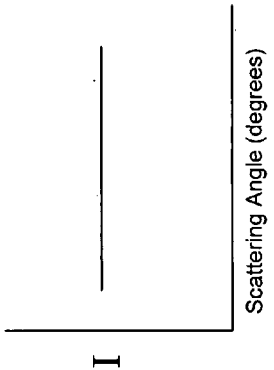
Figure 10A:
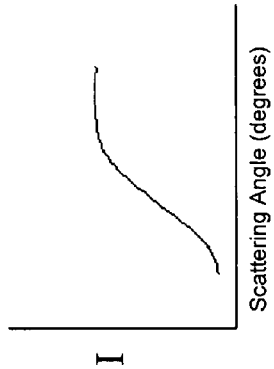

To determine the height and width of a structure that is larger than the width of the nanojet, the large structure is scanned. FIGS. 9a-c illustrate a photonic nanojet 906 scanning a large structure 902. Referring to FIGS. 9a-c, nanojet 906 is generated as an optical intensity pattern induced at a shadow-side surface of the dielectric microsphere 904. FIGS. 10a-c illustrate the corresponding graphs of the measured backscattered signatures generated from measurements in the FIGS. 9a-c photonic nanojet positions. The y-axis of the graphs in FIGS. 10a-c is Intensity and the x-axis is Scattering Angle, in degrees.

FIG. 9a illustrates nanojet 906 over the corner, or edge, of large structure 902. The measured backscattering signal in FIG. 10a corresponds to the nanojet 906 being positioned over a portion of structure 902 as depicted in FIG. 9a.

FIG. 9b illustrates nanojet 906 over the middle of the large structure 902. The measured backscattering signal in FIG. 10b corresponds to the nanojet 906 being over large structure 902 but not over the edge of the structure.

FIG. 9c illustrates nanojet 906 over the opposite corner, or edge, of the large structure 902. The measured backscattering signal in FIG. 10c corresponds to the nanojet 906 being positioned over a portion of structure 902 as depicted in FIG. 9c.

The location information from the positioning system, discussed above, can be combined with a set of measured backscattering signals (e.g., the signals illustrated in FIGS. 10a-c). This combined information can be utilized to determine the position, width, and height of large structure 902 in one direction.

The combined height information gathered from each point along the scan can be utilized to determine the height or various heights of structure 902 in one direction. Note the height of each portion of the structure can be determined from an individual signature. However, other portions of the structure might have varying heights. Therefore, it might be desirable to scan the entire structure to determine any varying heights of the structure.

Furthermore, similar scans in other directions can be conducted to determine other dimensions of structure 902. For example, assuming structure 902 is a square, a scan in a perpendicular direction can determine the other two edges of structure 902. Combining the location information from the positioning system with the edges identified in the perpendicular scan, the third dimension of structure 902 can also be determined.

This described embodiment should be taken as illustrative and not restrictive; there could be any number of measurements to determine the dimensions of various structures. There are also various scanning methods that can be employed such as tracing the edge of a structure.

Figure 2:
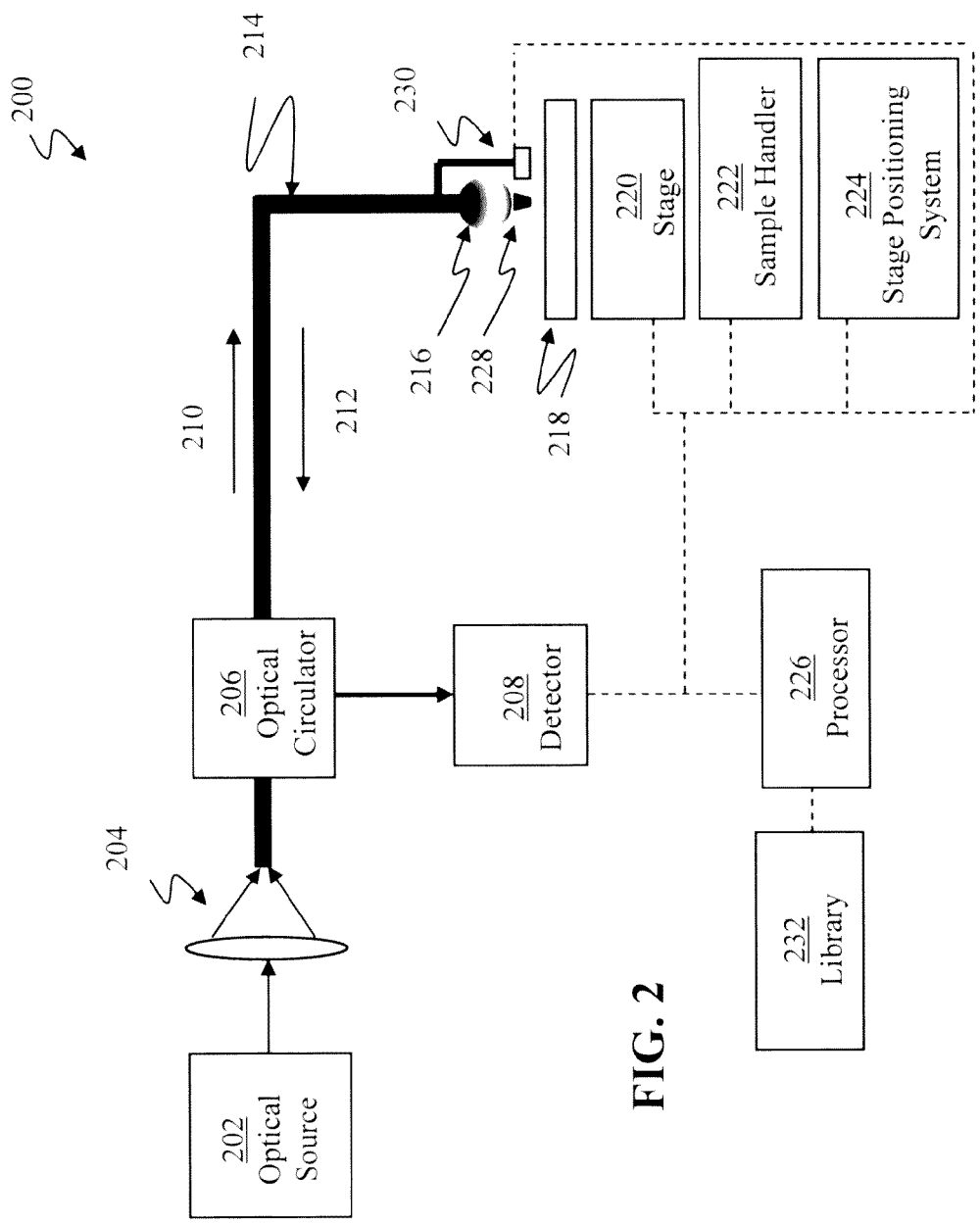
FIG. 2 is an architectural diagram of a photonic nanojet metrology system.

FIG. 2 is an architectural diagram of a photonic nanojet metrology system 200 for examining an inspection area on a semiconductor wafer. In one exemplary embodiment, photonic nanojet metrology system 200 includes an optical source 202, an optical lens 204, an optical fiber 214, a dielectric microsphere 216, a detector 208, and a processor 226.

As depicted in FIG. 2, a proximal end of the optical fiber 214 is coupled to the optical lens 204. A distal end of the optical fiber 214 is coupled to the dielectric microsphere 216. The distal end of the optical fiber 214 and the dielectric microphere 216 can be coupled using an adhesive. Alternatively, the dielectric microsphere can be directly fabricated by melting the tip of the optical fiber 214 with two counter-propagating $CO_2$ laser beams. The size of the microsphere can be accurately controlled by controlling the heating time and/or the laser power.

Figure 4:
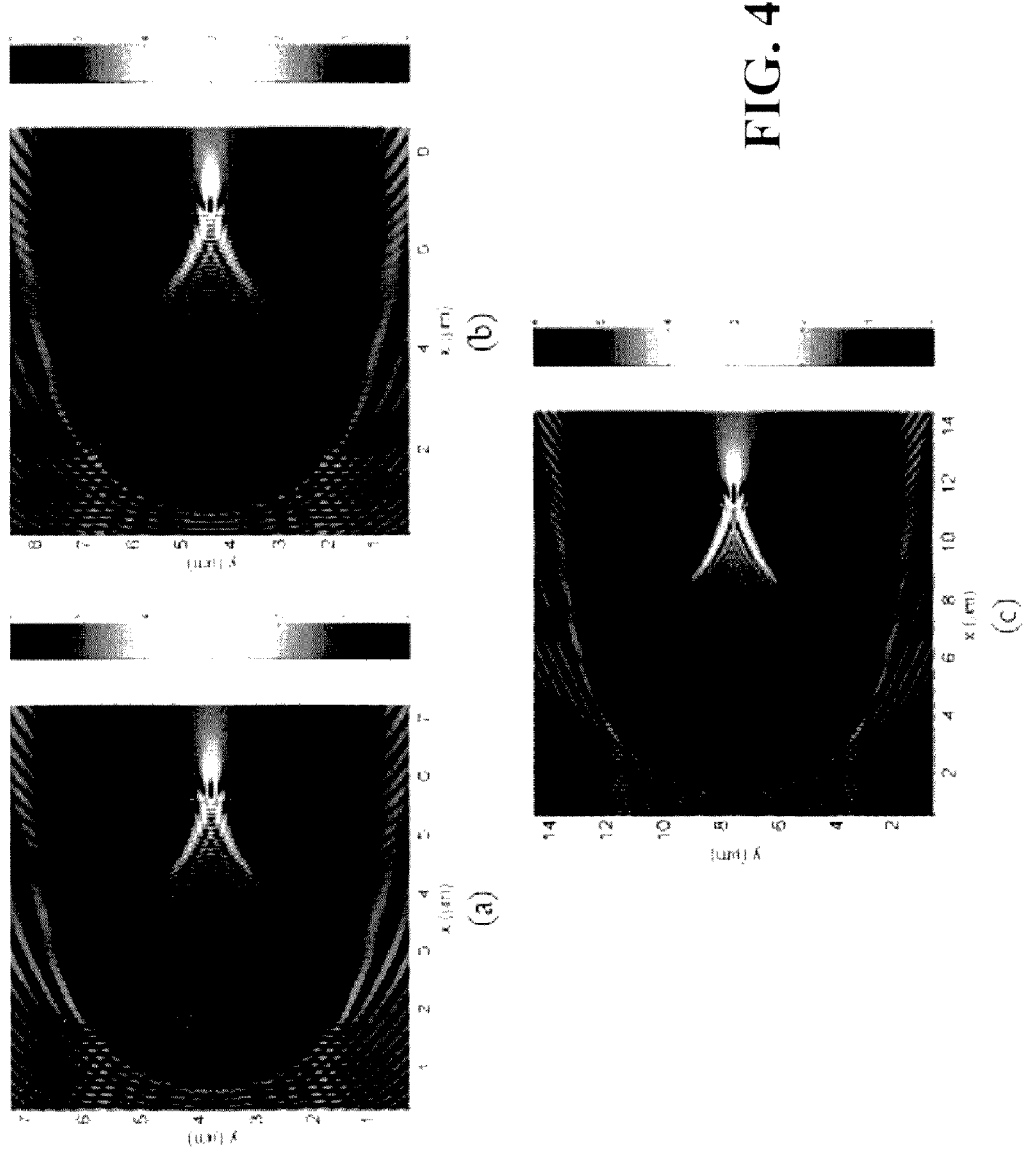
FIGS. 4a-c illustrate the thinning of a photonic nanojet.

When optical source 202, such as a continuous-wave laser, introduces light into optical fiber 214 through lens 204, the dielectric microphere 216 is illuminated by incoming light 210. As will be discussed in more detail below, a photonic nanojet 228 can then be generated as an optical intensity pattern induced at a shadow-side surface of the dielectric microsphere 216 (see also FIGS. 4 and 5). Dielectric microspheres are readily available from numerous commercial sources and proper selection of dielectric microspheres is discussed below.

An inspection area on wafer 218 is scanned with the photonic nanojet 228. As the photonic nanojet 228 interacts with the wafer surface, a portion of the incoming light 210 is retroreflected from the dielectric microsphere 216. The retroreflected light 212 is returned through optical fiber 214. The detector 208, which is connected to optical fiber 214, obtains a measurement of the retroreflected light 212. The processor 226, which is connected to the detector 208, can determine the existence of a structure in the inspection area with the obtained measurement of the retroreflected light 212. As described above, a library 232 of backscattered signatures can be used to determine the existence of a structure.

As depicted in FIG. 2, in the present exemplary embodiment, an optical circulator 206 can be disposed along optical fiber 214 between the optical lens 204 and the dielectric microsphere 216. As also depicted in FIG. 2, detector 208 is connected to optical fiber 214 through the optical circulator 206. Thus, it should be recognized that optical fiber 214 can include at least three segments (i.e., a first segment connecting the optical lens 204 to the optical circulator 206, a second segment connecting the optical circulator 206 to the dielectric microsphere 216, and a third segment connecting the optical circulator 206 to the detector 208). In the present exemplary embodiment, optical fiber 214 is a single-mode optical fiber.

As described above, wafer 218 can be moved relative to the photonic nanojet 228. Thus, in the present exemplary embodiment, photonic nanojet metrology system 200 includes a stage 220, a sample handler 222, and a stage positioning system 224. The sample handler 222 can be configured to automatically position and orient wafer 218 on the stage 220. The stage 220 can be configured to have six degrees of freedom including movement and rotation along the x-axis, y-axis, and z-axis. Fine alignment and positioning of the stage 220 can be controlled by stage positioning system 224, which can be a piezo nanopositioning system or other similar system.

In the present exemplary embodiment, the photonic nanojet metrology system 200 can include a range finder 230 adjacent to the dielectric microsphere 216. The range finder 230 is configured to measure the distance between the photonic nanojet 228 and the wafer 218. Alternatively, the backscattered signature measured by detector 208 can be used to measure the distance between the photonic nanojet 216 and the wafer 218. In particular, changes in the backscattered signature can be correlated to the distance between the photonic nanojet 216 and the wafer 218. After determining the distance between the photonic nanojet 228 and the wafer 218, the proper distance can then be maintained by the stage positioning system 224.

As depicted in FIG. 2, processor 226 can be connected to stage 220, sample handler 222, stage positioning system 224, and range finder 230. Process 226 can be configured to control the movement of wafer 218 using stage 220, sample handler 222, stage positioning system 224, and range finder 230. It should be recognized that processor 226 can be implemented as any number of processors or controllers.

Generation of Photonic Nanojets

Several calculations have been reported for the spatial distributions of the internal and near-external electromagnetic fields of plane-wave-illuminated infinite circular dielectric cylinders. See J. F. Owen, R. K. Chang, and P. W. Barber, "Internal electric field distributions of a dielectric cylinder at resonance wavelengths," Opt. Lett. 6, 540-542 (1981); and D. S. Benincasa, P. W. Barber, J.-Z. Zhang, W.-F. Hsieh, and R. K. Chang, "Spatial distribution of the internal and near-field intensities of large cylindrical and spherical scatters," Appl. Opt. 26, 1348-1356 (1987). These calculations have shown that high-intensity peaks can exist in both the internal and near-external fields along the incident axis even for nonresonant conditions. The location and the intensity of these near-field peaks depend upon the refractive index contrast between the cylinder and its surrounding medium, as well as the size parameter $x=ka=2\pi a/\lambda$ of the cylinder (where a is the radius and $\lambda$ is the incident wavelength). Interior and exterior caustics produced in the scattering of a diagonally incident plane wave by a circular cylinder have been examined using ray theory and the semi-classical limit of electromagnetic wave scattering theory. See C. L. Adler, J. A. Lock, B. R. Stone, and C. J. Garcia, "High-order interior caustics produced in scattering of a diagonally incident plane wave by a circular cylinder," J. Opt. Soc. Am. A 14, 1305-1315 (1997) and J. A. Lock, C. L. Adler, and E. A. Hovenac, "Exterior caustics produced in scattering of a diagonally incident plane wave by a circular cylinder: semiclassical scattering theory analysis," J. Opt. Soc. Am. A 17, 1846-1856 (2000).

Using high-resolution finite difference time domain (FDTD) numerical solutions of Maxwell's equations, the phenomenology of the generation of peaks of the internal and near-external fields of a plane-wave-illuminated dielectric cylinder have been examined. The two-dimensional (2-D) transverse magnetic (TM) case has been considered, i.e., where the incident magnetic field vector is perpendicular to the axis of an infinitely long cylinder of fixed cross section. Optical wavelengths of about 500 nm and cylinder diameters of about 5 µm have been investigated.

The FDTD computer code can be verified by calculating the differential scattering cross section of several homogeneous, isotropic, circular dielectric cylinders and comparing these results to the exact solution based on the separation-of-variables method. The perfectly matched layer (PML) absorbing boundary condition can be used in FDTD simulations to efficiently terminate the outer boundary of the computational lattice. With the FDTD space lattice having a uniform square cell size of 1.25 nm (finer than 1/100th dielectric wavelength for all computer runs), the results for the scattering cross section agree with the exact solution to within ±1.5 dB over the entire range of scattering angles. Typical computational dynamic ranges for this level of agreement were 60 dB.

Figure 3:
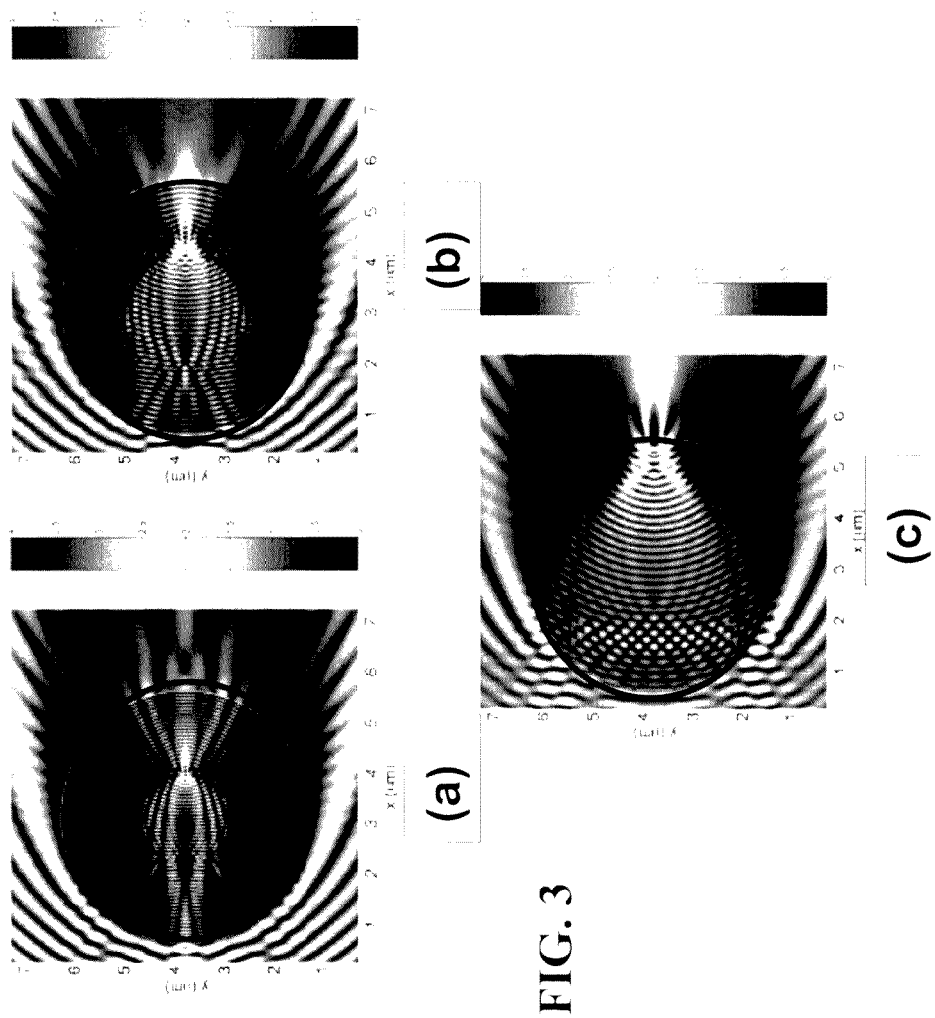
FIGS. 3a-c illustrate the evolution of a photonic nanojet.

FIG. 3 shows key results that illustrate the evolution of a photonic nanojet as the refractive index of the cylinder is changed relative to that of its surrounding medium. In this case, an infinite dielectric circular cylinder of diameter d=5 µm and refractive index n1 embedded within an infinite vacuum medium of refractive index of n2=1.0 is considered. The cylinder is normally illuminated by a rightward-propagating sinusoidal plane wave of wavelength $\lambda 2=500$ nm in medium 2. FIGS. 3a, 3b, and 3c visualize the FDTD-calculated envelope of the sinusoidal steady-state electric field for n1=3.5; 2.5, and 1.7, respectively. With each decrease of n1, it is evident that the internal electric-field peak shifts toward the shadow-side surface of the cylinder along the forward direction. The electric-field peak emerges from the shadow-side surface of the cylinder in FIG. 3(c) as a strong jet-like distribution. The photonic nanojet is neither evanescent nor diffracting. It has a length of about 900 nm (slightly less than $2\lambda 2$) and a full width at half maximum (FWHM) waist of about 250 nm ($0.5\lambda 2$). In terms of intensity (defined as squared electric field) distribution, it has a waist of about 200 nm, smaller than one-half wavelength. The emergence of a photonic nanojet from the shadow-side surface of this dielectric cylinder for n1~2 is primarily consistent with previous work on optical caustics generated by dielectric circular cylinders.

For scattering of a normally incident plane wave, the position of the cusp point focal line of the interior cusp caustics generated by dielectric circular cylinders embedded within an infinite vacuum medium is given by:

$$F=a(-1)^p/(2p-1-n_1). \quad (1)$$

The cusp point focal line of the exterior caustics consisting of a p=1 near-zone cylindrical aberration cusp caustic is given by:

$$f=an_1[2(n_1-1)] \quad (2)$$

a is the radius of the cylinder. $n_1$ is the refractive index of the cylinder. p denotes the number of internal chords of the ray trajectories, i.e., the family of rays that produces either an interior or exterior caustic has undergone p−1 internal reflections before the caustic is formed. Equations (1) and (2) may be used to approximately predict the position of the internal electric field peak and analyze the evolution of photonic nanojets.

The photonic nanojet shown in FIG. 3(c) can be made thinner by increasing the refractive index of the surrounding medium, which is equivalent to decreasing the wavelength of the incident light. This is shown in FIG. 4(a), which visualizes the FDTD-calculated envelope of the sinusoidal steady-state electric field distribution for the parameter set of d=5 μm, $n_1$=3.5, $n_2$=2.0, and $\lambda_2$=250 nm. The photonic nanojet of FIG. 4(a) has a waist of about 160 nm and a length of about 400 nm. In terms of intensity distribution, it has a waist of about 120 nm, smaller than one-half wavelength. It has been determined that photonic nanojets similar to that in FIG. 4(a) can be generated using a variety of combinations of d, $n_1$, $n_2$, and $\lambda_2$ provided that $n_1/n_2$ and $d/\lambda_2$ are not changed from the case of FIG. 4(a). This is shown in FIG. 4(b), which visualizes the FDTD-calculated envelope of the sinusoidal steady-state electric field distribution for the parameter set of d=6 μm, $n_1$=2.3275, $n_2$=1.33, and $\lambda_2$=300 nm. The photonic nanojet of FIG. 4(b) has a waist of about 200 nm and a length of about 500 nm. In terms of intensity distribution, it has a waist of about 130 nm, smaller than one-half wavelength. As another example, FIG. 4(c) illustrates the photonic nanojet produced by the parameter combination d=10 μm, $n_1$=2.3275, $n_2$=1.33, and $\lambda_2$=300 nm.

All parameters for this case are the same as for FIG. 4(b) except that the cylinder diameter is increased from 6 μm to 10 μm. Here, the nanojet has a length of about 1000 nm and a waist of about 200 nm. In terms of intensity distribution, it has a waist of about 140 nm, smaller than one-half wavelength. From these examples, the length of the photonic nanojet is effectively controlled by the size of the cylinder, whereas the waist of the photonic nanojet is determined by the incident wavelength in the surrounding medium.

The phenomenon of photonic nanojets can be readily extended from 2-D into 3-D, i.e., from dielectric microcylinders to microspheres. Calculations for the spatial distribution of the external near fields of a dielectric sphere are based upon Mie theory, the exact separation-of-variables eigenfunction solution for Maxwell's equations in spherical coordinates. It is assumed that the incident plane wave is linearly polarised along the x-axis and propagates along the z-axis. The origin of the coordinate system is taken at the centre of the sphere. Then, the incident wave of unity amplitude is expanded in spherical harmonics as:

$$E_{inc}(r) = \sum_{n=1}^{\infty} i^n\{(2n+1)/[n(n+1)]\}[M_{oln}^{(1)}(r) - iN_{eln}^{(1)}(r)] \quad (3)$$

M and N are the vector spherical harmonics. The expansion of the scattered field is given by:

$$E_{scat}(r) = \sum_{n=1}^{\infty} i^n\{(2n+1)/[n(n+1)]\}[ia_n N_{eln}^{(3)}(r) - b_n M_{oln}^{(3)}(r)] \quad (4)$$

$a_n$ and $b_n$ are the scattering coefficients. The superscripts appended to M and N denote the kind of spherical Bessel function. The total external intensity is defined by $$I(r)=|E_{inc}(r)+E_{scat}(r)|^2. I(r)=|E_{inc}(r)+E_{scat}(r)|^2.$$

Figure 5:
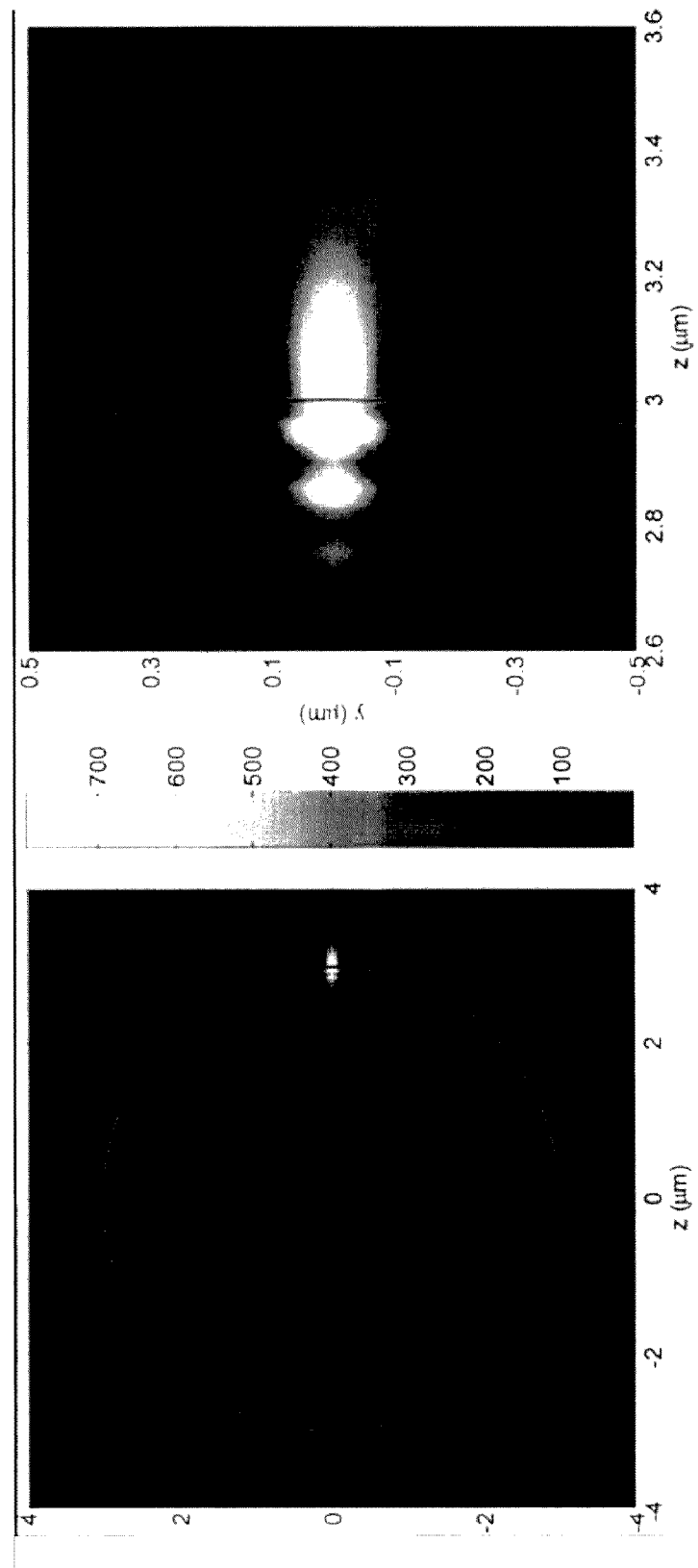
FIG. 5 illustrates the intensity distribution of a localized photonic nanojet.

FIG. 5 shows from the Mie-series calculation the intensity distribution of a localized photonic nanojet emerging along the direction of incidence from the shadow-side surface of a dielectric sphere of refractive index $N_1$=1.73 and radius a=3 μm. The sphere is assumed to be surrounded by vacuum of refractive index N=1, and illuminated at a wavelength of 300 nm. Two features of this photonic nanojet can be observed: (a) its intensity is up to 800 times that of the incident plane wave; and (b) it is neither evanescent nor diffracting. It has a length of more than 500 nm and a full-width at half-maximum (FWHM) waist of 130 nm, smaller than one-half wavelength (i.e., the diffraction limit).

Note that two parameters are critical in generating photonic nanojets. The size parameter x=ka=2πa/λ of the sphere controls the size (including width and length) of the nanojets, whereas the refractive index contrast between the sphere and its surrounding medium specifies the position of the localized intensity distribution.

Detection of Nanoparticles and Nano-Structures within the Photonic Nanojet

The photonic nanojet can strongly interact with nanoscale particles and structures and cause several orders-of-magnitude enhancements in the backscattered signature from the nanoscale structures. Further computational investigation of the photonic nanojets has confirmed that photonic nanojets do greatly enhance the effective backscattering of light by nanometer-scale dielectric particles located within the nanojets. This backscattering enhancement for nanoparticles exists for the nanojets generated by both microcylinders and microspheres. The only difference is that the order of magnitude of the enhancement is much higher in the case of microsphere-generated nanojets than in the case of microcylinder-generated nanojets.

Figure 6:
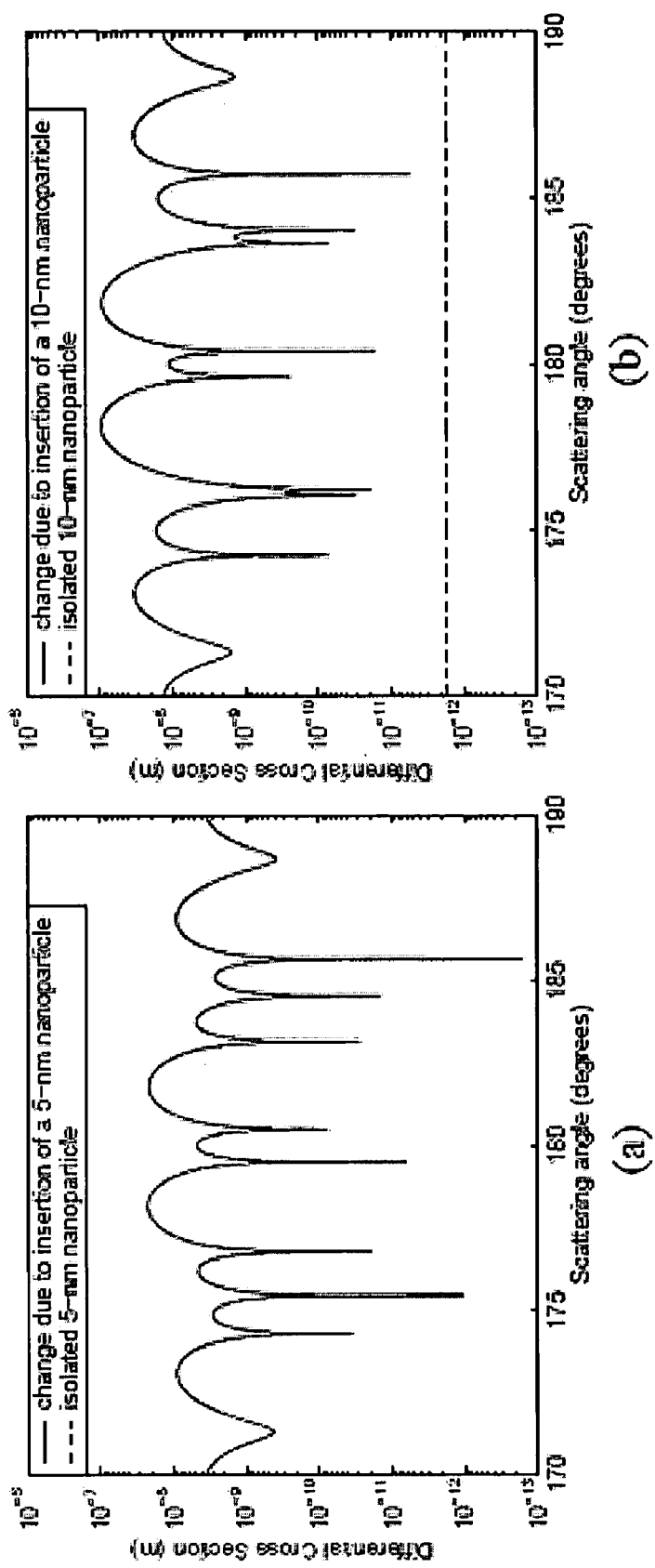
FIGS. 6a-b illustrate graphs of the absolute value of the change of the finite difference time domain (FDTD)-calculated differential scattering cross section.
Figure 7:
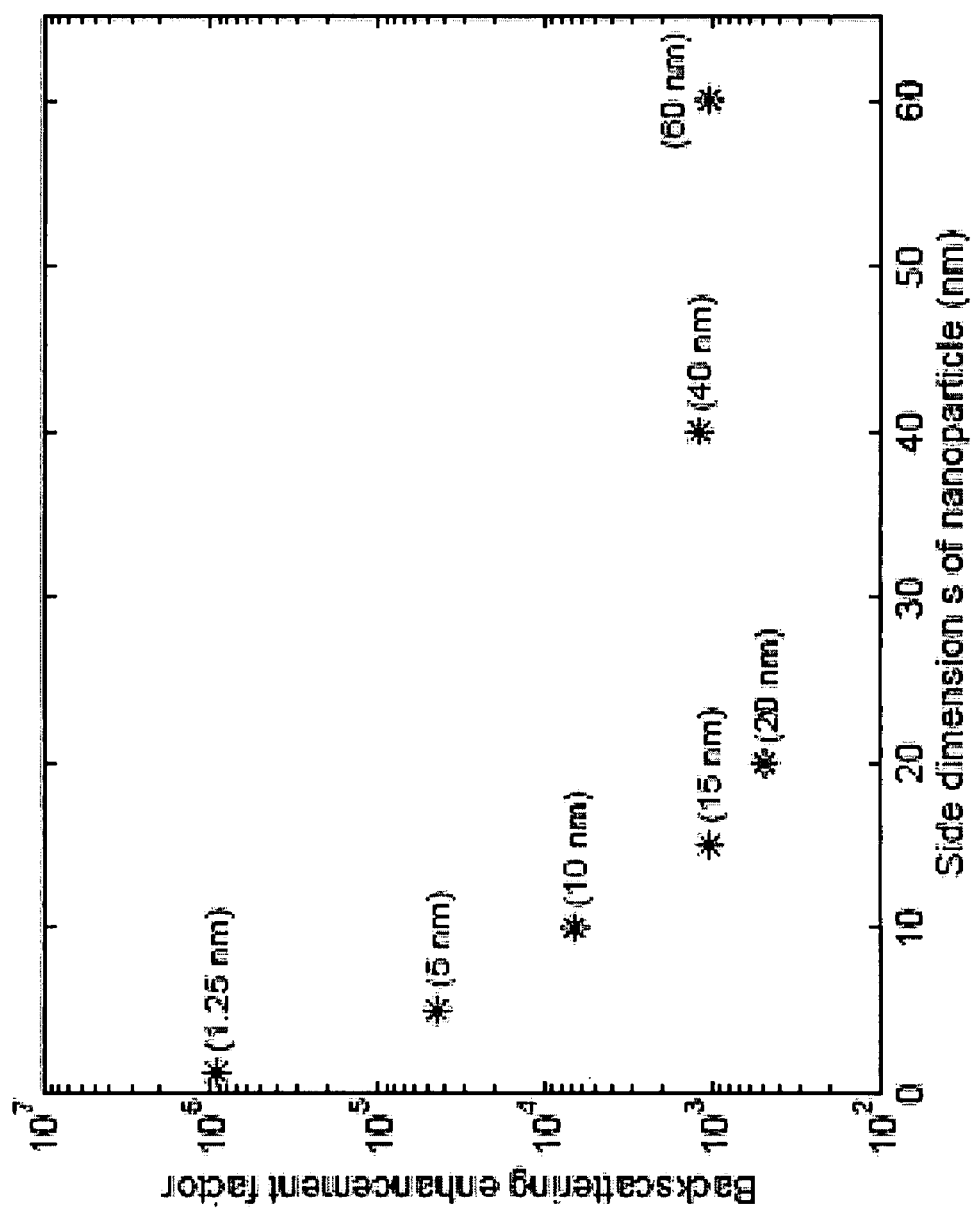
FIG. 7 illustrates a graph of the backscatter enhancement factor of a structure in a nanojet as a function of the size of the structure.

FIGS. 6 and 7 show the results of the FDTD numerical experiments that illustrate this phenomenon in microcylinders. In particular, the case of FIG. 4b (d=6 μm, $n_1$=2.3275, $n_2$=1.33, and $\lambda_2$=300 nm), with a square n=1.5 dielectric nanoparticle inserted at the center of the photonic nanojet on the surface of the 6-μm cylinder. A double-precision representation for data in the FDTD computer code was adopted in order to detect the nanoparticles with fine resolution. FIGS. 6a and 6b graph the absolute value of the change of the FDTD-calculated differential scattering cross section within ±10° of backscatter when a nanoparticle of side dimension s=5 nm and s=10 nm, respectively, is inserted at the center of the photonic nanojet. These figures also graph the corresponding differential scattering cross section of the isolated nanoparticle. It is seen that the effective backscattering cross section of each nanoparticle is enhanced by several orders of magnitude, specifically by ~$10^4$ for the 5-nm object and ~$10^3$ for the 10-nm object. In addition, the side lobes of the differential cross section near backscattering of the 10-nm object are wider than those of the 5-nm object. This may serve as another indicator for detecting nanoparticles of different sizes. FIG. 7 graphs the backscatter enhancement factor as a function of the size of the nanoparticle. It is apparent that the photonic nanojet created by the much larger 6-μm cylinder provides a dimensional increase in the effective backscattering cross section of the nanoparticle relative to the case where the nanoparticle is isolated.

The following discussions will concentrate on the microsphere-induced backscattering enhancement by nanoparticles, including but not limited to semiconductor features and dust or other particles that might contaminate the fabrication process.

It is well known that in the Rayleigh scattering limit of |m|x<<1, where m and x are the index of refraction and size parameter of a small particle, respectively, the Rayleigh scattering coefficient is given by $a_1 = (-2i/3)[(m^2-1)/(m^2-2)]x^3$. The corresponding scattering amplitude matrix elements are $S_1 = 3a_1/2$ and $S_2 = 3a_1 \cos\theta/2$, where $\theta$ is the scattering angle. It follows that the dimensionless scattering intensities $|S_1|^2$ and $|S_2|^2$ are proportional to $x^6$. The real scattering intensity I is related to the dimensionless scattering intensity $|S|^2$ by $I = |S|^2/k^2R^2$, where R is the distance from the particle to the detector. Therefore, the scattering intensities from a single isolated nanoparticle in the Rayleigh scattering limit are small and decline rapidly with the decrease of the particle size. Detecting such low-level scattering intensities from a single isolated nanoparticle is normally not possible using traditional optical instruments.

A properly chosen dielectric microcylinder or microsphere can create nanojets of localized optical fields significantly exceeding the excitation fields. Enhanced backscattering of light by a nanoparticle located within the nanojet can lead to enhancement factors between $10^7$-$10^{11}$ relative to classical Rayleigh scattering for particles of size between 100-1 nm, respectively. The phenomenon involves the mutual interactions of a micron-scale dielectric sphere and the nanoparticle positioned at a fixed surface-to-surface distance from the shadow side of the microsphere.

To develop quantitative data, the generalized multiparticle Mie (GMM) theory was applied, an extension of Mie theory, which is a rigorous analytical solution for light scattering by multiple spheres or particles. Generalized multiparticle Mie theory is further discussed in Y.-L. Xu, Appl. Opt. 34, 4573 (1995), which is incorporated by reference herein. Because GMM fully accounts for the interactive scattering effects of arbitrary configurations of multiple particles, it provides an efficient means to calculate the electromagnetic wave interactions of the microsphere and nanosphere.

In terms of the GMM theory, the interactive scattering coefficients for a microsphere coupled with a nanosphere are given by:

$$a_{mn}^M = a_n^M \left\{ p_{mn}^M - \sum_{v=1}^{\infty} \sum_{\mu=-v}^{v} [a_{\mu v}^N A_{mn}^{\mu v}(N, M) + b_{\mu v}^N B_{mn}^{\mu v}(N, M)] \right\} \quad (5)$$

$$b_{mn}^M = b_n^M \left\{ q_{mn}^M - \sum_{v=1}^{\infty} \sum_{\mu=-v}^{v} [a_{\mu v}^N A_{mn}^{\mu v}(N, M) + b_{\mu v}^N A_{mn}^{\mu v}(N, M)] \right\}. \quad (6)$$

The superscripts M and N denote the microsphere and nanosphere, respectively. $a_n^M$ and $b_n^M$ are the Mie scattering coefficients for the isolated microsphere. $p_{mn}^M$ and $q_{mn}^M$ are the expansion coefficients of the incident wave about the center of the microsphere (i.e., in the coordinate system of the microsphere). $a_{\mu v}^N$ and $b_{\mu v}^N$ are the interactive scattering coefficients for the nanosphere. $A_{mn}^{\mu v}(N,M)$ and $B_{mn}^{\mu v}(N,M)$ are the vector translation coefficients characterizing the transformation of the scattered waves from the nanosphere into the incident waves of the microsphere. It is noted that the first term on the right-hand side refers to the scattering of the initial incident wave, and the second term refers to the scattering of the fields scattered by the nanosphere.

Similarly, the interactive scattering coefficients for a nanosphere coupled with a microsphere are given by:

$$a_{mn}^N = a_n^N \left\{ p_{mn}^N - \sum_{v=1}^{\infty} \sum_{\mu=-v}^{v} [a_{\mu v}^M A_{mn}^{\mu v}(M, N) + b_{\mu v}^M B_{mn}^{\mu v}(M, N)] \right\}, \quad (7)$$

$$b_{mn}^N = b_n^N \left\{ q_{mn}^N - \sum_{v=1}^{\infty} \sum_{\mu=-v}^{v} [a_{\mu v}^M B_{mn}^{\mu v}(M, N) + b_{\mu v}^M A_{mn}^{\mu v}(M, N)] \right\}. \quad (8)$$

The total scattering coefficients for the bi-sphere system are given by $$a_{mn} = a_{mn}^M + a_{mn}^N \exp(-ikd \cos\theta), \quad (9)$$

$$b_{mn} = b_{mn}^M + b_{mn}^N \exp(-ikd \cos\theta), \quad (10)$$

where $k = 2\pi/\lambda$ is the wave number, d is the center-to-center distance between the microsphere and nanosphere, and $\theta$ is the scattering angle. It follows that the scattering amplitudes of the bi-sphere system are given by $$S_1(\theta) = \sum_{n=1}^{\infty} \sum_{m=-n}^{n} S_{mn}[a_{mn}\pi_{mn}(\cos\theta) + b_{mn}\tau_{mn}(\cos\theta)], \quad (11)$$

$$S_2(\theta) = \sum_{n=1}^{\infty} \sum_{m=-n}^{n} S_{mn}[a_{mn}\tau_{mn}(\cos\theta) + b_{mn}\pi_{mn}(\cos\theta)], \quad (12)$$

where $$S_{mn} = (2n+1)\frac{(n-m)!}{(n+m)!}, \quad \pi_{mn}(\cos\theta) = \frac{m}{\sin\theta}P_n^m(\cos\theta),$$

$$\tau_{mn}(\cos\theta), \quad \tau_{mn}(\cos\theta) = \frac{d}{d\theta}P_n^m(\cos\theta);$$

and $P_n^m(\cos\theta)$ is the associated Legendre function of the first kind and of degree n and order m (n and m are integers). In the backward direction, $S_1(180°) = -S_2(180°)$, and the dimensionless backscattering intensity of the bi-sphere system is given by $$|S(180°)|^2 = |S_1(180°)|^2 = |-S_2(180°)|^2.$$

Using the GMM theory, the dimensionless backscattering intensity of the microsphere-nanosphere system can be calculated where a nanosphere with an index of refraction m=1.1 is located in the photonic nanojet of FIG. 5. The surface-to-surface distance between the microsphere and nanosphere is 25 nm. This backscattering intensity is denoted as $|S|^2$. The backscattering intensity was also calculated for the isolated microsphere, denoted as $|S^M|^2$. The perturbation in the backscattering intensity of the microsphere introduced by the nanosphere is therefore defined as:

$$\delta|S^M|^2 = ||S|^2 - |S^M|^2|, \qquad (13)$$

which represents the enhanced backscattering intensity of the nanosphere due to its interaction with the microsphere.

FIG. 8(a) compares the enhanced backscattering intensity of Eq. (13) (solid red line) with the classical Rayleigh backscattering intensity of the isolated nanosphere, $|S^N|^2$ (dashed blue line), as a function of the size parameter of the nanosphere. FIG. 8(a) also shows the lens focusing effect of the microsphere (dash-dotted green line), i.e., due to the illumination of the nanosphere by the high-intensity photonic nanojet. FIG. 8(b) graphs the ratio $$\frac{\delta|S^M|^2}{|S^N|^2}$$

i.e., the backscattering enhancement factor (solid red line). Note that log-log scales are used because of the wide dynamic range of the independent and dependent variables.

Figure 8:
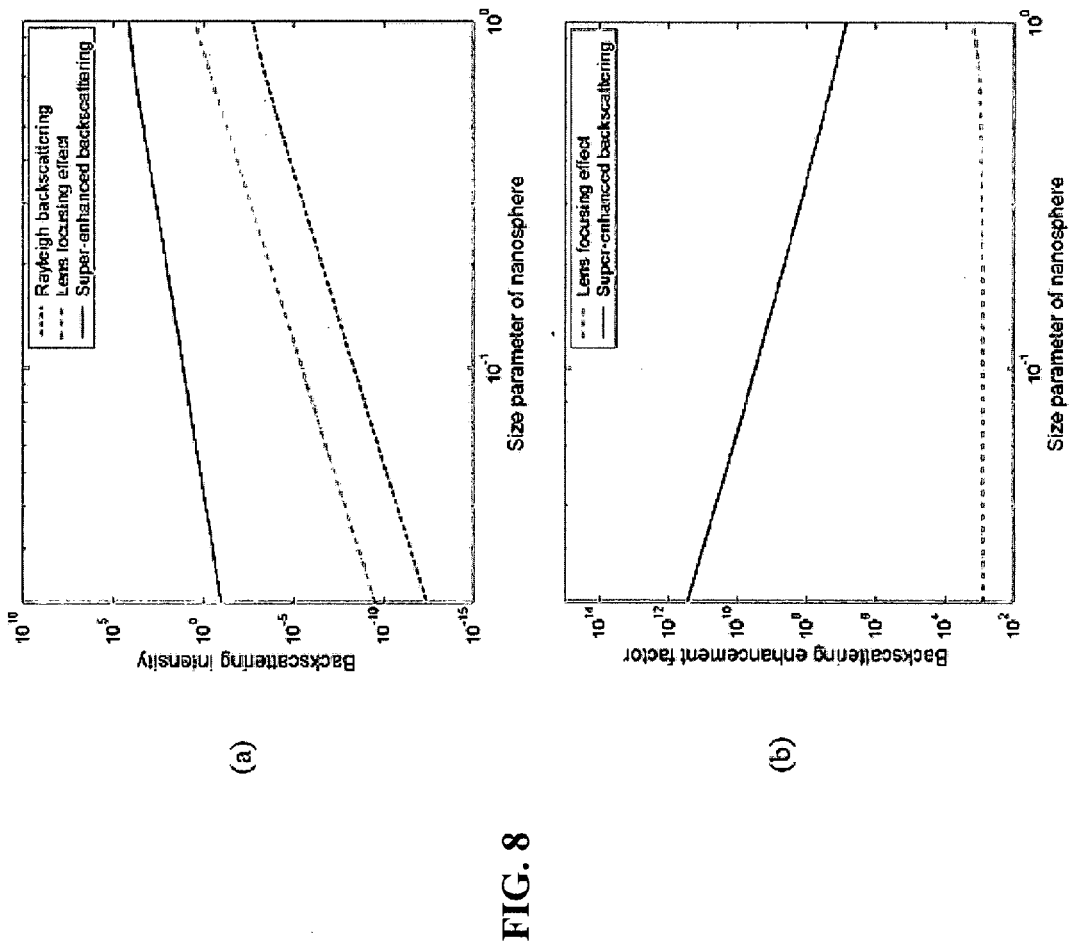
FIG. 8a illustrates a graph of the comparison of the enhanced backscattering intensity of a nanosphere with the lens focusing effect of the microsphere and the classical Rayleigh scattering intensity as a function of size parameter.
FIG. 8b illustrates a graph of the backscattering enhancement factor, i.e., ratio of the enhanced backscattering intensity to the classical Rayleigh scattering intensity, as a function of the size parameter.

Three features can be observed from FIG. 8. First, the enhanced backscattering intensity of the nanosphere is 7-11 orders of magnitude higher than its classical Rayleigh scattering intensity. Second, the lens focusing effect of the microsphere can account for at most three orders of magnitude of this enhancement. Therefore, the observed super-enhancement phenomenon is significantly distinguished from a traditional microlens. Third, the enhanced backscattering intensity is proportional to a lower power of the size parameter of the nanosphere compared with the classical Rayleigh scattering intensity.

Since the lens focusing effect of the microsphere by itself can not account for the enhanced backscattering of the nanosphere, additional physical mechanisms are required to completely explain the phenomenon. In order to identify these mechanisms, a perturbation analysis can be conducted based on the fundamental GMM theory. The perturbations in the scattering coefficients of the microsphere due to the presence of the nanosphere in the photonic nanojet are given by the second terms in Eqs. (5) and (6), i.e., $$\delta a_{mn}^M = -a_n^M \sum_{\nu=1}^{\infty} \sum_{\mu=-\nu}^{\nu} [a_{\mu\nu}^N A_{mn}^{\mu\nu}(N,M) + b_{\mu\nu}^N B_{mn}^{\mu\nu}(N,M)] \qquad (14a)$$

$$\delta b_{mn}^M = -b_n^M \sum_{\nu=1}^{\infty} \sum_{\mu=-\nu}^{\nu} [a_{\mu\nu}^N B_{mn}^{\mu\nu}(N,M) + b_{\mu\nu}^N A_{mn}^{\mu\nu}(N,M)]. \qquad (14b)$$

In Eq. (14), $a_{\mu\nu}^N$ and $b_{\mu\nu}^N$ are the interactive scattering coefficients for the nanosphere characterizing the scattering of both the original incident waves and the secondary waves scattered by the microsphere. To obtain a simplified form of $a_{\mu\nu}^N$ and $b_{\mu\nu}^N$, the internal electric field intensity distribution of the nanojet-illuminated nanosphere in the microsphere-nanosphere system is first calculated using the GMM theory. The calculations show that the internal intensity distribution of the nanojet-illuminated nanosphere is elevated by a factor of about 800 relative to that resulting from plane-wave illumination, and is nearly uniform within the nanosphere.

Next the far-field scattering intensity of the nanojet-illuminated nanosphere coupled with the microsphere based on its internal electric field distribution is calculated. This calculation can be performed by weighting the internal electric field of the nanosphere with the free-space Green's function and integrating over the volume of the nanosphere. It is noted that this far-field scattering intensity represents the lens focusing effect of the microsphere, as previously seen in FIG. 8 (green dash-dotted line).

Based on this analysis, the interactive scattering coefficients of the nanosphere coupled with the microsphere can be approximately written as:

$$a_{mn}^N \approx \sqrt{\tilde{I}_{jet}/I_0} a_n^N p_{mn}^N, \qquad (15a)$$

$$b_{mn}^N \approx \sqrt{\tilde{I}_{jet}/I_0} b_n^N q_{mn}^N, \qquad (15b)$$

where $$\tilde{I}_{jet} = \frac{\iint_{\pi r_N^2} I_{jet} d\sigma}{\pi r_N^2}$$

is the intensity of the photonic nanojet averaged over the transverse cross section of the nanosphere, $I_0$ is the intensity of the original incident wave, and $a_n^N$ and $b_n^N$ are the Mie scattering coefficients of an isolated nanosphere. In the Rayleigh scattering limit of $|m|x \ll 1$, the higher-order Mie scattering coefficients in Eq. (15) involving terms of order $x^5$ and higher are negligible. As a result, Eq. (14) can be simplified considerably:

$$\delta a_{mn}^M = -a_n^M \sqrt{\tilde{I}_{jet}/I_0} \, a_1^N \sum_{\mu=-1}^{1} p_{\mu 1}^N A_{mn}^{\mu 1}(N,M) \qquad (16a)$$

$$\delta b_{mn}^M = -b_n^M \sqrt{\tilde{I}_{jet}/I_0} \, a_1^N \sum_{\mu=-1}^{1} p_{\mu 1}^N B_{mn}^{\mu 1}(N,M) \qquad (16b)$$

where $a_1^N$ is the Rayleigh scattering coefficient of an isolated nanosphere and is given by $$a_1^N = (-2i/3)[(m^2-1)/(m^2+2)]x^3.$$

The physical meaning of Eq. (16) is as follows: (1) $a_1^N$ represents the Rayleigh scattering by an isolated nanosphere; (2) $\sqrt{\tilde{I}_{jet}/I_0} a_1^N$ embodies enhanced scattering from the nanosphere due to the lens focusing effect of the microsphere; (3) the enhanced scattered fields from the nanosphere due to the lens focusing effect of the microsphere are transformed into the incident fields of the microsphere, and this transformation is accounted for by the vector translation coefficients $A_{mn}^{\mu 1}$ and $B_{mn}^{\mu 1}$; and (4) the transformed scattered fields from the nanosphere are scattered again and collected by the microsphere in the backward direction, which is described by the Mie scattering coefficients of the microsphere $a_n^M$ and $b_n^M$.

On the basis of Eq. (16), the perturbation in the backscattering intensity of the microsphere introduced by a nanosphere located in the photonic nanojet can be analyzed. In the backward direction, $|S(180°)|^2 = |S_1(180°)|^2 = |-S_2(180°)|^2$. The dimensionless backscattering intensity of the microsphere-nanosphere system can be written as:

$$|S(180°)|^2 = S_2(180°)|^2 \quad (17)$$

$$= S_2(180°) \cdot S_2^*(180°)$$

$$= \left\{\sum_{n=1}^{\infty}\sum_{m=-n}^{n} S_{mn}[a_{mn}\tau_{mn} + b_{mn}\pi_{mn}]\right\} \cdot$$

$$\left\{\sum_{n'=1}^{\infty}\sum_{m'=-n'}^{n'} S_{m'n'}[a^*_{m'n'}\tau_{m'n'} + b^*_{m'n'}\pi_{m'n'}]\right\}$$

$$= \sum_{n=1}^{\infty}\sum_{m=-n}^{n}\sum_{n'=1}^{\infty}\sum_{m'=-n'}^{n'} S_{mn}S_{m'n'}[a_{mn}a^*_{m'n'}\tau_{mn}\tau_{m'n'} +$$

$$a_{mn}b^*_{m'n'}\tau_{mn}\pi_{m'n'} + a^*_{m'n'}b_{mn}\tau_{m'n'}\pi_{mn} +$$

$$b_{mn}b^*_{m'n'}\pi_{mn}\pi_{m'n'}]$$

$$= |S^M|^2 + \delta|S^M|^2,$$

where the superscript * stands for the complex conjugate, $a_{mn}$ and $b_{mn}$ are given by Eqs. (9) and (10), $|S^M|^2$ represents the dimensionless backscattering intensity for the isolated microsphere given by:

$$|S^M|^2 = \sum_{n=1}^{\infty}\sum_{m=-n}^{n}\sum_{n'=1}^{\infty}\sum_{m'=-n'}^{n'} S_{mn}S_{m'n'}[a_n^M p_{mn}^M a_{n'}^{M*} p_{m'n'}^{M*}\tau_{mn}\tau_{m'n'} + \quad (18)$$

$$a_{mn}p_{mn}^M b_{n'}^{M*} q_{m'n'}^{M*}\tau_{mn}\pi_{m'n'} +$$

$$a_{n'}^{M*} p_{m'n'}^{M*} b_n^M q_{mn}\tau_{m'n'}\pi_{mn} + b_n^M q_{mn}^M b_{n'}^{M*} q_{m'n'}^{M*}\pi_{mn}\pi_{m'n'}],$$

and $\delta|S^M|^2$ represents the perturbation in the dimensionless backscattering intensity of the microsphere introduced by the nanosphere located in the photonic nanojet.

Substituting Eqs. (9), (10), and (16) into $\delta|S^M|^2$ and neglecting higher-order terms involving products of $\delta a_{mn}^M$ and $\delta b_{mn}^M$ yields:

$$\delta|S^M|^2 \approx (2/3)[(m^2-1)/(m^2+2)]\sqrt{\overline{I}_{jet}/I_0}F^M(kd)x^3, \quad (19)$$

where x is the size parameter of a nanosphere, $F^M$ is a function of kd for a given microsphere, and kd is given by:

$$kd = \frac{2\pi}{\lambda}(r_M + r_N + \Delta), \quad (20)$$

where $r_M$ is the radius of the microsphere, $r_N$ is the radius of the nanosphere, and $\Delta$ is the surface-to-surface distance between the microsphere and nanosphere. For a small nanosphere in the Rayleigh limit, $$kd \approx \frac{2\pi}{\lambda}(r_M + \Delta). \quad (21)$$

Therefore, $F^M$(kd) is approximately a constant for a fixed wavelength and a fixed surface-to-surface distance between the microsphere and nanosphere. As a result, $\delta|S^M|^2$ is approximately proportional to the third power of the size parameter of the nanosphere. For the microsphere, $F^M$(kd) has an order of magnitude $10^4$.

It is noted that the nanojet-inducing dielectric microsphere analyzed herein differs significantly from the traditional microlens in terms of physical mechanisms. It is a backscattering-detection system as opposed to an imaging lens system. As a result, it is not affected by the usual diffraction limit. The effective backscattering of the nearby nanosphere is enhanced by the mutual interaction between the nano and microspheres. The nanoparticle is first excited by the photonic nanojet emerging from the microsphere, and its scattering intensity is elevated by two orders of magnitudes, as determined by the intensity of the nanojet. The scattered fields generated by the nanojet-excited nanoparticle propagate into the microsphere, which leads to non-Rayleigh backscattering of light by the nanoparticle as part of the combined system. This interaction elevates the backscattered intensity from the nanojet-excited nanoparticle by four to nine additional orders of magnitude.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

We claim:

1. A method of examining an inspection area of a semiconductor wafer comprising:
   generating a photonic nanojet, wherein the photonic nanojet is an optical intensity pattern induced at a shadow-side surface of a dielectric microsphere;
   scanning the inspection area with the photonic nanojet;
   obtaining a measurement of retroreflected light from the dielectric microsphere as the inspection area is scanned with the photonic nanojet; and
   determining the existence of a structure in the inspection area with the obtained measurement of the retroreflected light.

2. The method of claim 1, further comprising:
   determining the location of the structure in the inspection area.

3. The method of claim 1, further comprising:
   determining the height and width of the structure in the inspection area with the obtained measurement of the retroreflected light.

4. The method of claim 3, wherein determining the height and width of the structure comprises:
   generating a measured backscattered signature with the measurement of retroreflected light;
   determining a matching backscattered signature for the measured backscattered signature from a library of backscattered signatures and corresponding heights and widths of structures; and
   determining the height and width of the structure in the inspection area to be the corresponding height and width of the matching backscattered signature from the library.

5. The method of claim 1, wherein the photonic nanojet is generated with a continuous-wave laser.

6. The method of claim 1, wherein the structure is selected from the group consisting of: a gate, line, contact hole, via, drain, and periodic structure.

7. The method of claim 1, wherein the structure is a contaminating particle.

8. A computer-readable storage medium containing computer executable instructions for causing a computer to examine an inspection area of a semiconductor wafer, comprising instructions for:

obtaining a measurement of retroreflected light from a dielectric microsphere as the inspection area is scanned with a photonic nanojet, wherein the photonic nanojet is an optical intensity pattern induced at a shadow-side surface of the dielectric microsphere; and determining the existence of a structure in the inspection area with the obtained measurement of the retroreflected light.

9. The computer-readable storage medium of claim 8, further comprising instructions for:

determining the location of the structure in the inspection area.

10. The computer-readable storage medium of claim 8, further comprising instructions for:

determining the height and width of the structure in the inspection area with the obtained measurement of the retroreflected light.

11. The computer-readable storage medium of claim 10, wherein determining the height and width of the structure comprises instructions for:

generating a measured backscattered signature with the measurement of retroreflected light;

determining a matching backscattered signature for the measured backscattered signature from a library of backscattered signatures and corresponding heights and widths of structures; and determining the height and width of the structure in the inspection area to be the corresponding height and width of the matching backscattered signature from the library.

12. A system for examining an inspection area of a semiconductor wafer for the existence of a structure, the system comprising:

an optical source;

an optical fiber;

an optical lens coupled to a proximal end of the optical fiber;

a dielectric microsphere coupled to a distal end of the optical fiber, wherein a photonic nanojet is generated as an optical intensity pattern induced at a shadow-side surface of the dielectric microsphere;

a detector connected to the optical fiber, wherein the detector is configured to obtain a measurement of retroreflected light reflected from the inspection area, induced by the dielectric microsphere; and a processor connected to the detector, wherein the processor is configured to determine the existence of a structure in the inspection area with the obtained measurement of the retroreflected light.

13. The system of claim 12, further comprising:

an optical circulator connected to the optical fiber, wherein the detector is connected to the optical fiber through the optical circulator, and wherein the optical circulator is configured to send the retroreflected light transmitted through the optical fiber from the dielectric microscope to the detector.

14. The system of claim 12, wherein the system further comprises:

a range finder disposed adjacent to the dielectric microsphere, wherein the range finder is configured to measure the distance between the wafer and the photonic nanojet.

15. The system of claim 9, wherein the processor is further configured to determine the height and width of the structure in the inspection area.

16. The system of claim 15, further comprising:

a library of backscattered signatures and corresponding heights and widths of structures.

17. The system of claim 16, wherein the processor is configured to:

generate a measured backscattered signature with the measurement of retroreflected light;

determine a matching backscattered signature for the measured backscattered signature from the library; and determine the height and width of the structure in the inspection area to be the corresponding height and width of the matching backscattered signature from the library.

18. The system of claim 12, wherein the optical source is a continuous-wave laser.

19. The system of claim 12, wherein the structure is selected from the group consisting of a gate, line, contact hole, via, drain, and periodic structure.

20. The system of claim 12, wherein the structure is a contaminating particle.

* * * * *